United States Patent [19]

Shieh et al.

[11] Patent Number: 5,565,226
[45] Date of Patent: * Oct. 15, 1996

[54] IMMOBILIZED ENZYME FOR REMOVAL OF RESIDUAL CYCLODEXTRIN

[75] Inventors: Wen Shieh; Allan Hedges, both of Crown Point, Ind.

[73] Assignee: American Maize-Products Company, Hammond, Ind.

[*] Notice: The term of this patent shall not extend beyond the expiration date of Pat. No. 5,532,005.

[21] Appl. No.: 268,803

[22] Filed: Jun. 29, 1994

Related U.S. Application Data

[63] Continuation-in-part of Ser. No. 891,224, May 29, 1992.

[51] Int. Cl.$^6$ ....................................................... A23L 1/00
[52] U.S. Cl. .................... 426/7; 426/28; 426/32; 426/34; 426/42; 426/45; 426/47; 426/48; 426/49; 426/52; 435/262
[58] Field of Search ..................... 426/7, 32, 33, 426/34, 44, 45, 47, 49, 51, 52, 28, 42, 48, 55, 56; 435/262

[56] References Cited

U.S. PATENT DOCUMENTS 4,880,573  11/1989  Courregelongue .
4,980,180  12/1990  Cully et al. .
5,342,633   8/1994  Cully et al. .................. 426/47

FOREIGN PATENT DOCUMENTS 8341391  3/1992  Australia .
2050031  2/1992  Canada .
2657623  8/1991  France .
4230104  3/1994  Germany .

OTHER PUBLICATIONS

"Cyclodextrin News" vol. 3, No. 10, Jun. 1989, entitled Removing Undesired Components from Food.
Preliminary Product Information, Novo Enzyme Process Division, Maltogenase TM, 2 pages.
Kirk–Othmer Encyclopedia of Chemical Technology, 3rd Edition, vol. 9, Enzymes, Immobilized, pp. 148–172.

*Primary Examiner*—Leslie Wong
*Attorney, Agent, or Firm*—Lucas & Just

[57] ABSTRACT

The immobilized enzyme for removal of residual cyclodextrins is either a combination of an alpha-amylase and a CGTase which has been immobilized or a fungal alpha-amylase which has been immobilized. In addition to either the fungal alpha-amylase or the CGTase and alpha-amylase, a debranching enzyme can also be employed. When using a debranched enzyme, the debranched enzyme is also immobilized. By using the immobilized enzyme, the step of inactivating the enzyme is eliminated and the contamination due to the inactivated enzyme is also eliminated.

13 Claims, No Drawings

IMMOBILIZED ENZYME FOR REMOVAL OF RESIDUAL CYCLODEXTRIN

CROSS-REFERENCES TO RELATED APPLICATIONS

This is a continuation-in-part of U.S. patent application Ser. No. 891,224 filed May 29, 1992.

BACKGROUND OF THE INVENTION

The present invention relates to cyclodextrin and, more specifically, to the removal of residual cyclodextrin from a system without contaminating the system with enzyme. The present invention is especially applicable to food systems.

In recent years cyclodextrin has been used to remove unwanted substances from a number of different systems, especially food systems. For example, cyclodextrin has been used to remove cholesterol from eggs and butter; caffeine from chocolate, tea and coffee; phenylalanine from protein hydrolysates; and phenolic compounds, pigments and bitter components from fruit juice. Typically, this removal process entails a two-step process of first mixing cyclodextrin or an aqueous slurry of cyclodextrin with the food system to form a complex between the cyclodextrin and the unwanted substance; and subsequently removing the complex from the food system. Conventionally, the complex is then separated into its individual components and the cyclodextrin recycled to be used again in the removal process.

One of the problems associated with this process is that a small amount of cyclodextrin is left in the system after the complex is removed from the system. The source of this residual cyclodextrin is twofold, unrecovered complex and unremoved, uncomplexed cyclodextrin. Since the complexation process is an equilibrium reaction, an excess amount of cyclodextrin is mixed into the system to push the equilibrium toward complexation. This inevitably means that a certain amount of cyclodextrin is in the uncomplexed state when the complex is removed from the system. Some of the uncomplexed cyclodextrin is left behind in the system when the complex is removed from the system, thus accounting for the unremoved, uncomplexed cyclodextrin.

The other source of residual cyclodextrin, unremoved complex, is due to the inefficiency of the removal of the complex from the system. In some food systems, for example coffee, the complex is removed as a precipitate from solution. Oftentimes soluble or readily suspendable complexes are not removed from the system. In other cases, such as butter, the complexes are removed by washing the butter with water. In these instances, not all of the complex is washed away. In either case, washing or precipitation, the unrecovered complex goes through an equilibrium reaction wherein the guest and cyclodextrin move between a complexed and uncomplexed state. Thus, the unremoved complex is another source of residual cyclodextrin. No matter what the source, the residual cyclodextrin must be removed from the system. The term residual cyclodextrin as used in the specification and claims means cyclodextrin which remains in the system after the majority of the complex has been removed from the system.

It has been suggested that the residual cyclodextrin be removed from egg yolk or egg yolk plasma by adding a soluble enzyme to the egg yolk and then incubating the system to allow the enzyme to decompose the cyclodextrin. Specifically, U.S. Pat. No. 4,980,180 teaches using a soluble alpha-amylase derived from the microorganisms of the group *Aspergillus niger, Aspergillus oryzae, Bacillus polymyxa, Bacillus coagulans,* Flavobacterium, or domestic hog pancreas amylase to remove cyclodextrin from eggs. A problem associated with soluble alpha amylases which have been used to hydrolyze cyclodextrin is that they do not hydrolyze all cyclodextrin. Specifically, it has been found that they do not hydrolyze branched cyclodextrin and they do not hydrolyze all of the alpha cyclodextrin.

It has also been suggested to use a combination of alpha-amylase and cyclodextrin glycosyl transferase (CGTase) to hydrolyze the residual cyclodextrin. Such a combination has been found to hydrolyze virtually all of the residual cyclodextrin.

Whether using one or two enzymes to remove residual cyclodextrin, these enzymes remain in the system and must be inactivated. Typically, the enzymes are inactivated by a conventional means such as high temperature or extremely high or low pH. Such an inactivation step is not acceptable in food systems like milk and eggs because such an inactivation step can change the physical properties of the treated food. Additionally, the inactivated enzyme remains in the system and acts as a contaminant to the system. There is a need for a process wherein residual cyclodextrin is removed from a system without the need to go through a deleterious step to inactivate the enzyme and without contaminating the system with inactivated enzyme.

SUMMARY OF THE INVENTION

It has now been discovered that residual cyclodextrin can be removed without contaminating a system with inactivated enzyme and without subjecting the system to an enzyme inactivation step. The process of the present invention comprises treating the system containing residual cyclodextrin with an immobilized enzyme in the presence of water to hydrolyze the residual cyclodextrin. Because the enzyme is immobilized, it is easily separated from the system and can be used repeatedly, thereby providing a cost saving to the user.

The use of the immobilized enzyme in accordance with the present invention not only removes the residual cyclodextrin from the system but avoids contaminating the system with inactivated enzyme.

More specifically, the immobilized enzyme for use in accordance with the present invention is either a fungal alpha-amylase or a combination of at least two separate enzymes wherein one of the enzymes is an immobilized cyclodextrin glycosyl transferase (CGTase) and the other enzyme is an immobilized amylase.

DESCRIPTION OF THE PREFERRED EMBODIMENTS

In a preferred embodiment of the present invention, the system containing the residual cyclodextrin is also treated with an immobilized debranching enzyme in order to remove the branches from residual branched cyclodextrin. Branched cyclodextrin is more resistant to hydrolysis by immobilized fungal alpha-amylase and the combined immobilized CGTase/amylase than non-branched cyclodextrin. The debranching enzyme removes the branches from the branched cyclodextrin and makes the cyclodextrin more susceptible to hydrolysis by the other enzymes. The use of the immobilized debranching enzyme preferably precedes the fungal alpha-amylase or CGTase/amylase combination because certain amylases such as glucoamylase and fungal alpha-amylase will work on the branch itself to reduce the branch to a glucosyl stub, and the glucosyl is resistant to debranching enzymes.

The fungal alpha-amylases used in the present invention are derived from microorganisms such as *Aspergillus niger* and *Aspergillus oryzae*. A good commercial source of fungal alpha-amylase is sold under the name FUNGAMYL® by Novo Industri A/S.

Suitable sources of cyclodextrin glycosyl transferase include *Bacillus macerans, Bacillus megaterium, Bacillus circulans,* and *Bacillus stearothermophilus*. Good results have been obtained with *Bacillus stearothermophilus*.

When using the combination of CGTase and amylase, suitable amylases include alpha-amylase, beta-amylase, and glucoamylase. The alpha-amylase can be either bacterial, fungal or mammalian. Suitable sources of alpha amylases include *Bacillus polymyxa, Bacillus coagulans, Bacillus licheniformis, Bacillus subtilus, Aspergillus niger, Aspergillus oryzae*, Flavobacterium, or domestic hog pancreatic amylase. Suitable beta amylases are obtained from Barley malt, soy bean, and wheat. Suitable glucoamylases are obtained from *Aspergillus niger, Aspergillus oryzae, Rhizopus oryzae* and *Rhizopus nivens*. The preferred glucoamylase is *Aspergillus niger* and *Aspergillus oryzae*.

The combination of a CGTase and an amylase wherein the amylase is a fungal alpha-amylase has the fastest reaction rate compared to the other combinations of CGTase and other amylases or fungal alpha-amylase alone; however, the combined CGTase and fungal alpha-amylase is also the most costly at the present time. Additionally, it has been found, at this time, that the fungal alpha-amylase alone has a faster reaction rate than the combined CGTase and bacterial alpha-amylase. Therefore, fungal alpha-amylase alone is preferred over the combination of CGTase and fungal alpha-amylase or the combination of a CGTase and another amylase.

Suitable debranching enzymes are pullulanase, isoamylase and any other endo-enzymes which hydrolyze only alpha D-(1-6) glucosidic linkages of starch. Preferably, pullulanase is used as the debranching enzyme.

In order to prepare immobilized enzyme in accordance with the present invention, any conventional procedure may be employed. Typically, an inert support is used to which the enzyme is bonded.

In the case of fungal alpha-amylase and the other amylases, good results can be obtained by bonding the enzyme to a support such as diatomaceous earth, cellulose, agrose, and silica gel. The procedure for bonding the fungal alpha-amylase consists of polyethyleneimine reaction product with 1,2-dichloroethane and glutaraldehyde as a cross-linking agent for the immobilized enzyme.

In the case of the CGTase, the enzyme can be bonded to a support of diatomaceous earth, cellulose, agrose, and silica gel by any conventional technique, such as that used for the fungal alpha-amylase.

There are a number of immobilized amylases available in the marketplace which can be used in accordance with the present invention. For example, glucoamylase covalently bonded to glass, glucoamylase bonded to DEAE-cellulose, glucoamylase covalently bonded to silica, and fungal alpha-amylase bonded to diatomaceous earth.

In order to treat the system with immobilized enzyme to remove the residual cyclodextrin in accordance with the present invention, any conventional process can be used which treats a system with an immobilized enzyme. The process can be continuous or batch. For example, columns such as a packed bed, or a fluidized bed reactor can be used. Alternatively, a tank can be used with an impeller or a continuous flow stirred tank reactor. Additionally, the immobilized enzyme can be packed in a basket surrounded by a fine screen and immersed in a reactor while the system is stirred. Which of these reactors is employed depends on the flow characteristics of the system being treated as well as the stability of the enzyme on the support. There are different chemical bonds between the support and the enzyme and the chemical bonding has an effect on the stability of the enzyme.

When the combined immobilized CGTase and amylase are employed in accordance with the present invention, the reactor is packed with both immobilized enzymes on a support.

In order to treat the system with the immobilized enzyme, the pH and temperature of the system are adjusted to optimum conditions for the enzyme and the system being treated. As can be appreciated, both the optimum pH and temperature for the system must be taken into consideration so as not to have a deleterious effect on the system. Preferably, the pH is adjusted to about 5.0 to about 7.0 and the temperature is adjusted to about 30° C. to about 60° C. More preferably, a temperature of about 50° C. and a pH of about 6 is used. These are the preferred pH and temperature for fungal alpha-amylase and the combined CGTase/amylase.

Good results for treating the system with immobilized enzyme have been accomplished in a batch operation by adding immobilized enzyme to the system at the optimum pH and temperature; and maintaining the system at that temperature and pH for a period of about 10 minutes to about 24 hours. The system is agitated during treatment to uniformly mix the system and enzyme. The system was adjusted to the appropriate pH prior to treatment with either acid or base. More preferably, the system is treated for about 10 minutes to about 1 hour and, more preferably, about 10 minutes to about 30 minutes. The time of treatment will be dependent upon the microbial situation. As a general rule, growth of microbes should be avoided.

Consideration of the enzymes employed and the system itself dictates the treatment conditions. Additionally, the temperature will preferably be adjusted to optimize the activity of the enzymes in the system without having a deleterious effect on the system.

Treatment of the system is carried out with conventional equipment and in the presence of water. Treatment is preferably conducted under agitation using conventional equipment. Alternatively, one or more of the enzymes are immobilized and the system is passed through the immobilized enzyme.

The present invention is especially suited for food systems such as egg or dairy which have been subject to a decholesterolization step wherein beta cyclodextrin has been added to complex with the cholesterol. In such a food system, the process of the present invention is employed to remove residual cyclodextrin after separation of the complexed cyclodextrin/cholesterol without contaminating the food system with enzyme. The present invention works not only on cyclodextrin and branched cyclodextrin, but also on modified cyclodextrin with low degrees of substitution.

The process of the present invention has also been found to be useful in removing residual cyclodextrin from maltodextrin which is a by-product from the formation of cyclodextrin.

The amount of immobilized enzyme used to treat a food system to remove residual cyclodextrins depends substantially upon the amount of residual cyclodextrins that are in the system, the system itself, and the activity of the enzyme. Preferably, about 0.005% to about 0.05% by weight immobilized enzyme fungal alpha-amylase or, for the combination of CGTase/amylase, about 0.005% to about 0.05% CGTase with about 0.005% to about 0.05% amylase. The amount of debranching enzyme used is preferably about 0.001% to about 0.05% by weight. These weight percents are based on the weight of enzyme to weight of residual cyclodextrin.

It is known that enzymes from different sources have different reactive rates. Applicants have found that the preferred amount of enzyme used in the present invention is the amount of enzyme that can digest a set amount of residual beta-cyclodextrin in a system within about 30 minutes. In other words, the preferred amount of enzyme used in the present invention is dependent upon the enzyme activity in the given system. The optimum amount of enzyme for each system varies from system to system and enzyme to enzyme. In fact, as will be seen in the examples herein, two different sources of the fungal alpha-amylase have different reaction rates in the same system treated under the same conditions.

Applicants have found that the preferred amount of enzyme for a given system can digest about 8,000 to 9,000 ppms of residual beta-cyclodextrin contained in about 100 gram sample of said system when said sample is treated at about 50° C. and a pH of about 6 for a period of about 30 minutes. The system comprises a slurry of foodstuffs (egg yolk) and water having a solids content of about 25% by weight and having about 8,000 to about 9,000 ppms of residual beta-cyclodextrin. After about 30 minutes no detectable beta-cyclodextrin remained in the sample. The amount of beta-cyclodextrin in the system is determined by conventional techniques, using conventional equipment, namely HPLC. Such a test is conducted in a 250 ml flask while the flask is agitated.

The treatment with the immobilized debranching enzyme is preferably done prior to the treatment with the fungal alpha-amylase or the combination of CGTase/amylase. However, the treatment with immobilized debranching enzyme can be done at the same time as the other immobilized enzyme. It will be appreciated by those of skill in the art that most commercial sources of cyclodextrin contain a small portion of branched cyclodextrin.

These and other aspects of the present invention may be more fully understood by reference to the following examples.

EXAMPLE 1

This example illustrates the use of two sources of immobilized fungal alpha-amylase to decompose residual cyclodextrin from the same food system, namely egg yolk, under the same conditions.

Two samples of 100 grams aqueous solution of egg yolk (25% solids) which contained 8000 to 9000 ppms of residual beta-cyclodextrin were treated with different immobilized fungal alpha-amylase enzyme. Both enzymes were immobilized onto an inert substrate. For example, Enzyme A was immobilized on a diatomaceous earth. Both enzymes were obtained from Aspergillus oryzae. In this example, 20 grams of immobilized Enzyme A was used, while 40 grams of Enzyme B was used. It should be understood that these weights included the enzyme and the inert support to which the enzyme was bonded. The treatment was conducted by placing the 100 gram sample and respective enzyme into a 250 ml flask and the flasks were shaken throughout the treatment step. Both treatments were conducted at a pH of 6 and at a temperature of 50° C. Samples from both flasks were withdrawn at varying time intervals as listed below to determine the amount of residual cyclodextrin remaining in the system.

|  | Concentration of Beta-Cyclodextrin (PPM) | |
| --- | --- | --- |
| Time | Enzyme A | Enzyme B |
| 0 | 8000–9000 | 8000–9000 |
| 15 minutes | 699 | 541 |
| 30 minutes | None detected | None detected |
| 1 hour | None detected | None detected |

The amount of beta cyclodextrin present in the egg system was determined by conventional chromatography (HPLC). Additionally, a conventional Phadebus Amylase Test Method was used to measure the amount of enzyme in the system after treatment. No enzyme was found in the system after treatment in accordance with the present invention.

EXAMPLE 2

This example illustrates using a combined alpha amylase and CGTase to remove residual beta cyclodextrin from an egg system.

A 100 gram sample of egg yolk which contained 8000–9000 ppms of residual beta-cyclodextrin is treated with a combination of immobilized bacterial alpha-amylase and CGTase in the same manner as taught in Example 1 above. The pH of the solution is 6 and the temperature is 50° C. during treatment. After completing the treatment, neither residual cyclodextrin nor enzyme is present in the system.

It will be understood that the claims are intended to cover all changes and modifications of the preferred embodiments of the invention herein chosen for the purpose of illustration which do not constitute a departure from the spirit and scope of the invention.

What is claimed is:

1. A process for removal of residual cyclodextrin from a system containing such residual cyclodextrin comprising the steps of:

(a) treating a system comprising residual cyclodextrin and water with an immobilized enzyme, said immobilized enzyme being a combination of CGTase and an amylase, at a pH of about 5.0 to about 7.0 and a temperature of about 30° C. to about 60° C. for a period of about 10 minutes to about 24 hours; and (b) recovering a system substantially free of residual cyclodextrin and free of contaminating enzyme.

2. The process of claim 1 wherein said amylase is a fungal alpha-amylase derived from Aspergillus niger, or Aspergillus oryzae.

3. The process of claim 1 wherein the amylase is selected from the group consisting of alpha amylase, beta amylase and glucoamylase.

4. The process of claim 1 wherein the system is a food system selected from the group consisting of eggs, dairy, meat, suet, lard, fruit juice, coffee, chocolate, and tea.

5. The process of claim 1 wherein the system is a starch hydrolysate or a protein hydrolysate.

6. The process of claim 1 wherein prior to treating the system with said immobilized enzyme, the system is treated with an immobilized debranching enzyme at a pH of about 4 to about 6, at a temperature of about 50° C. and for a period of time of about 10 minutes to about 1 hour.

7. The process of claim 1 wherein an immobilized debranching enzyme is used to treat the system simultaneously with the immobilized enzyme.

8. A process for removal of residual cyclodextrin from a system containing such residual cyclodextrin comprising the steps of:

(a) treating a system comprising residual cyclodextrin and water with an immobilized fungal alpha-amylase enzyme at a pH of about 5.0 to about 7.0 and a temperature of about 30° C. to about 60° C. for a period of about 10 minutes to about 24 hours; and (b) recovering a system substantially free of residual cyclodextrin and free of contaminating enzyme.

9. The process of claim 8 wherein said fungal alpha-amylase is derived from *Aspergillus niger*, or *Aspergillus oryzae*.

10. The process of claim 8 wherein the system is a food system selected from the group consisting of eggs, dairy, meat, suet, lard, fruit juice, coffee, chocolate, and tea.

11. The process of claim 8 wherein the system is a starch hydrolysate or a protein hydrolysate.

12. The process of claim 8 wherein prior to treating the system with said immobilized enzyme, the system is treated with an immobilized debranching enzyme at a pH of about 4 to about 6, at a temperature of about 50° C. and for a period of time of about 10 minutes to about 1 hour.

13. The process of claim 8 wherein an immobilized debranching enzyme is used to treat fungal alpha-amylase enzyme.

* * * * *